United States Patent [19]

Kaehler et al.

[11] Patent Number: 4,687,635

[45] Date of Patent: Aug. 18, 1987

[54] POROUS LOAD VAPOR STERILIZATION CYCLE

[75] Inventors: Kristine M. Kaehler, Erie; Ronald P. Krahe, Girard; Peter T. Miraldi; Richard A. McBride, both of Erie, all of Pa.

[73] Assignee: American Sterilizer Company, Erie, Pa.

[21] Appl. No.: 658,396

[22] Filed: Oct. 5, 1984

[51] Int. Cl.⁴ ............................................. A61L 2/20
[52] U.S. Cl. ........................................ 422/26; 422/3; 422/33; 422/110; 422/111
[58] Field of Search .................... 422/26, 27, 108-111, 422/3, 34, 33

[56] References Cited

U.S. PATENT DOCUMENTS

| | | | |
|---|---|---|---|
| 3,068,064 | 12/1962 | McDonald | 422/34 X |
| 3,402,991 | 9/1968 | Henfrey | 422/105 |
| 3,409,389 | 11/1968 | Bjork | 422/26 |
| 3,454,352 | 7/1969 | Lamboy et al. | 422/26 X |
| 3,589,861 | 6/1971 | Gunther | 422/33 X |
| 3,967,494 | 7/1976 | Joslyn | 422/26 X |
| 4,164,538 | 8/1979 | Young et al. | 422/26 |
| 4,239,731 | 12/1980 | Gillis et al. | 422/27 X |
| 4,263,258 | 4/1981 | Kalasek | 422/26 X |
| 4,294,804 | 10/1981 | Baran | 422/27 X |
| 4,309,381 | 1/1982 | Chamberlain et al. | |
| 4,335,071 | 6/1982 | Thornton | 422/26 |
| 4,372,916 | 2/1983 | Chamberlain et al. | 422/26 X |

FOREIGN PATENT DOCUMENTS

| | | | |
|---|---|---|---|
| 32426 | 11/1927 | France | 422/26 |
| 542554 | 1/1942 | United Kingdom | 422/26 |

Primary Examiner—David L. Lacey
Assistant Examiner—William R. Johnson
Attorney, Agent, or Firm—Robert D. Yeager; Edward L. Pencoske

[57] ABSTRACT

A steam sterilization cycle having a conditioning stage, a sterilizing stage, a drying stage and an air admission stage which provides maximum removal of entrapped air from full or partial porous loads. The conditioning stage includes a plurality of pressure/vacuum pulses. The final vacuum pulses are deeper than the initial pulses. The sterilizing stage includes a diffusion dwell come-up which gradually increases the temperature and pressure of the chamber to the predetermined sterilization temperature by a sequence of pressure rises followed by pressure plateaus which permit substantially complete steam penetration of the load and substantial equalization of the actual load temperature and the temperature sensed by the sterilizer controls and substantially eliminates superheating the chamber. The cycle may also include a step for detecting and reacting to unacceptable levels of noncondensable gas present in the chamber during the sterilization stage.

12 Claims, 5 Drawing Figures

POROUS LOAD VAPOR STERILIZATION CYCLE

BACKGROUND OF THE INVENTION

1. Field of the Invention

The present invention relates to a method for processing a load, and, more particularly, to a method for steam processing porous loads.

2. Description of the Prior Art

In order to effectively sterilize porous loads, such as fabric packs, the air trapped within the interstices of the load must be withdrawn prior to the stabilization phase of the sterilization cycle so that the steam can contact every portion of the load. Air pockets within the load block the entrance of steam. Furthermore, air leaks within the sterilization chamber are detrimental to sterilization.

Means for detecting the presence of air in the chamber during the sterilization phase and method of removing air from the chamber and the load prior to the sterilization phase have been suggested. For example, Henfrey U.S. Pat. No. 3,402,991, (the "Henfrey Patent") which issued on Sept. 24, 1968, describes a load simulator which simulates the conditions in the sterilization chamber, specifically, the steam-air proportions within the chamber. The Henfrey load simulator includes a temperature sensing means which responds to the steam-air conditions and actuates controls which reduce the period of sterilization. The load simulator described by the Henfrey Patent operates on the premise that even in those instances where there is an air leak, that sterilization of the load will eventually occur if a certain temperature is detected by the temperature sensing means in the load simulator. Until a predetermined temperature is sensed the sterilization phase continues.

Young et al. U.S. Pat. No. 4,164,538, (the "Young Patent") which issued on Aug. 14, 1979, and is incorporated herein by reference, describes a method for conditioning the sterilization chamber prior to the sterilization phase of the cycle. A sequence of cyclic pressure pulses is described wherein the chamber is alternately evacuated to both a minimum time of at least one minute and a minimum pressure of at least ten inches Hg, and then pressurized to a level below the desired sterilization pressure. The Young Patent states that minimal fabric loads may require longer or deeper vacuum treatment for air removal during conditioning because the pressure drop in the chamber is rapid. Full fabric loads on the other hand, according to the Young Patent, require a longer exposure time to bring the vacuum down to the ten inch Hg level.

It has been observed, however, that full fabric loads can retain more air, even when the chamber is evacuated to ten inches Hg over a relatively long period of time, than is retained by minimal fabric loads when the chamber is evacuated over a shorter period to a level of ten inches Hg or less. For purposes of detecting unacceptable levels of air in the chamber during the sterilization phase, therefore, the proportion of steam to air will not be the same for full and minimal loads at the start of the phase.

Following the cyclic pressure pulses of the conditioning phase, the sterilization method described in the Young Patent proceeds by introducing and maintaining steam at a desired level for an effective time. During the sterilization phase, the ambient chamber temperature is constantly monitored by a temperature probe in the drain line. If air remain in the fabric load, the temperature of the load will be lower than the ambient temperature in the chamber for a given point in time. Although the load temperature rises, it lags behind the ambient chamber temperature. Thus, there is a lag between the temperature sensed by the probe and the actual temperature of the load. Because the length and accuracy of the sterilization cycle are often dependent upon the temperature sensed by the chamber drain line probe, the cycle may be concluded before the load has been subjected to the sterilizing temperature for a full cycle.

There is a need for a more thorough method of removing the air from porous loads to substantially eliminate the disparities in the steam-air proportions in a chamber between minimal and full porous loads. There is a further need to substantially eliminate the lag between the temperature sensed and the actual load temperature. Finally, there is a need for detecting even small quantities of air in a chamber which can compromise the effectiveness of the sterilization phase.

SUMMARY OF THE INVENTION

The present invention provides a method of vapor processing of porous loads which satisfies the need for substantially eliminating noncondensable gases from porous loads and for substantially eliminating the lag time between the actual load temperature and the chamber temperature sensed. The present invention also increases the sensitivity of air detection apparatus. The present invention is particularly well suited for vapor sterilization.

The present invention includes a method for increasing the temperature and pressure within a sealable chamber wherein a porous load is disposed for processing and from both of which noncondensable gases have been substantially removed. The method includes, after sealing the chamber, subjecting the chamber to a gradual pressurization period wherein a condensable vapor having transferable latent heat, such as steam, is so injected into the chamber that the gradual pressurization period is sufficient to so gradually elevate the temperature and pressure within the chamber to a predetermined temperature effective for processing, or sterilizing, the porous load that the opportunity for substantially surpassing the predetermined temperature is substantially eliminated. Furthermore, the gradual pressurization period is also sufficient to permit such penetration of the porous load by the vapor that the porous load reaches a general equilibrium with the vapor in the chamber at least at about the same time as the chamber reaches the predetermined temperature.

The gradual pressurization period may be a plurality of pressurization steps. Each pressurization step may include a pressure rise during which vapor is injected into the chamber, followed by a pressure plateau during which the chamber is isolated to permit the vapor to penetrate the porous load to displace any noncondensable gas within the load and to permit the chamber and load temperatures and pressures to stabilize.

The method may be preceded by a conditioning stage for substantially removing noncondensable gases, such as air, from the chamber and the load. The conditioning stage includes subjecting the chamber and the load to a plurality of cyclic pressure pulses below an upper pressure level related to the predetermined temperature by injecting the vapor into the chamber and evacuating the chamber. Each cyclic pressure pulse includes an evacuating phase during which the pressure in the chamber is decreasing and a vapor injecting phase during which the pressure is increasing. The evacuating phases of the plurality of pressure pulses include at least one initial evacuating phase during which the pressure in the chamber is decreased to a first lower pressure level and at least one final evacuating phase during which the pressure in the chamber is decreased to a second lower pressure level which is lower than the first lower pressure level.

The sterilization cycle of the present invention includes at least a conditioning stage, as described above, and a sterilization stage. It preferably also includes a drying stage and an air admission stage following the drying stage.

The sterilization cycle is practiced in a sterilizer having a sealable pressure chamber and associated piping. The piping may include a remote section, preferably surrounded by atmospheric air. The cycle may include a step for detecting and responding to unacceptable levels of noncondensable gas in a fluid in the chamber during the sterilization stage. The fluid includes at least the vapor.

The step for detecting and responding to unacceptable levels of noncondensable gas includes communicating the fluid within the chamber to the remote section during the sterilization stage of the cycle. The vapor in the fluid is so condensed and the condensate so discharged from the remote section as the fluid is communicated to the remote section that any noncondensable gas within the fluid accumulates in the remote section where its temperature is measured. The noncondensable gas temperature so measured is employed to automatically fail the sterilization cycle when the nonconensable gas temperature so measured equals a preselected temperature effective for indicating the presence of a predetermined unacceptable level of noncondensable gas in the chamber.

BRIEF DESCRIPTION OF THE DRAWINGS

The following detailed description of the preferred embodiment can better be understood if reference is made to the drawings in which.

DETAILED DESCRIPTION OF THE PREFERRED EMBODIMENT

Figure 1:
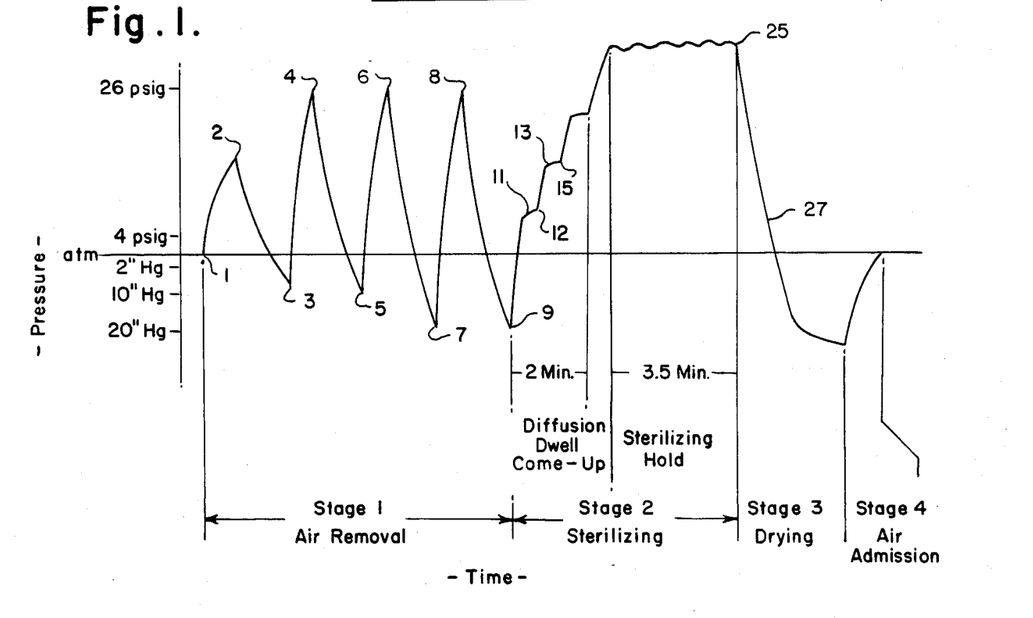
FIG. 1 is a graph of the preferred embodiment of the sterilization cycle of the present invention.

The method of the present invention is shown in graphic form in FIG. 1. Stage 1 is a conditioning stage, during which air is removed, stage 2 is a sterilizing stage, stage 3 is a drying stage and stage 4 is an air admission stage. Stage 1 includes a sequence of pressure/vacuum pulses which will be explained in more detail hereinbelow. Stage 3 includes a diffusion dwell pressure come-up which provides a gradual pressurization increase, which is shown as a stepped increase in chamber temperature which allows the chamber and load temperature to stabilize. Stage 2 also includes a sterilization hold period in which the chamber is pressurized with steam to the desired temperature and maintained at that temperature for a predetermined, preset period of time.

Figure 2:
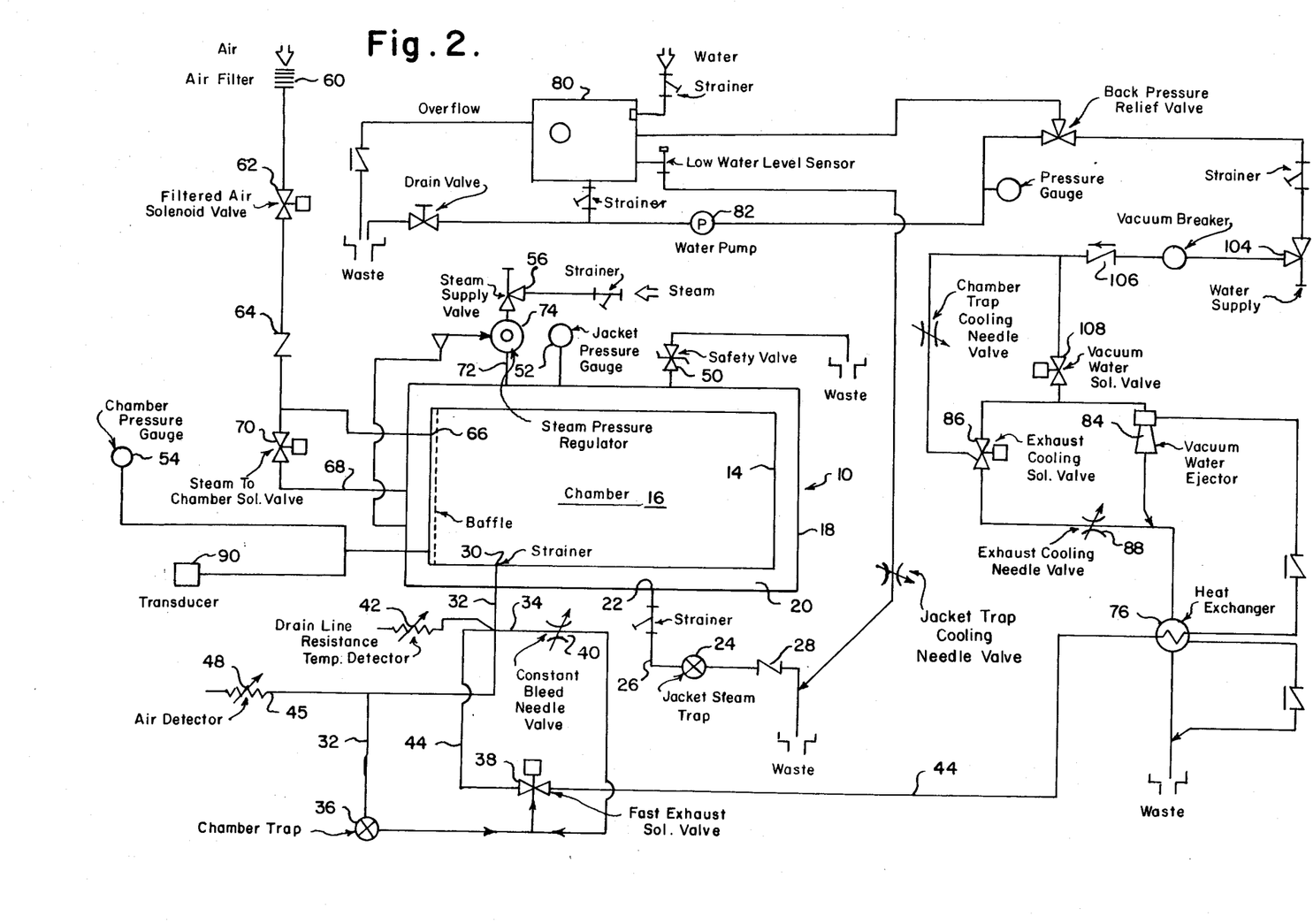
FIG. 2 is a schematic diagram of a sterilizer and piping arrangement in which the sterilization method of the present invention may be practiced.
Figure 3:
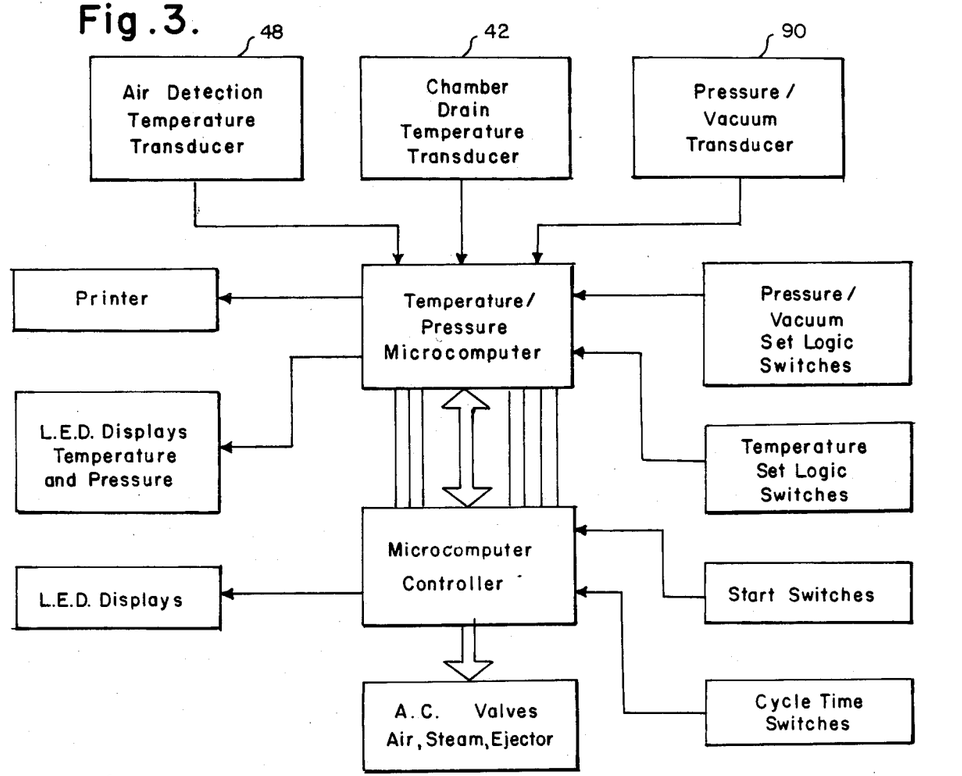
FIG. 3 is a schematic diagram of a control system which may be employed to effect the method of the present invention.

The invention can be practiced in a conventional vapor sterilizer of suitable size and configuration. FIG. 2 schematically illustrates one possible sterilization chamber and piping arrangement. FIG. 3 schematically illustrates one possible control system for the sterilizer. Those skilled in the art will recognize, however, that other piping and control arrangements can be used to effectively practice the method of the present invention and that the specific arrangements shown and decribed herein do not limit the scope of the present invention. Any condensable vapor capable of transferring latent heat sufficient for processing a load of porous goods for a desired purpose will suffice. Steam, either alone or in mixture with other condensable sterilizing agents, is contemplated as the vapor of choice in the preferred embodiment of the present invention.

Referring to FIG. 2, there is shown a double walled sterilizer 10 which includes an inner walled structure 14 and an outer walled structure 18. A sterilization, or pressure chamber 16 is defined within the inner walled structure 14. A vapor jacket 20 is defined between the inner walled structure 14 and the outer walled structure 18. A door (not shown) opens chamber 16 to the external environment. The sterilizer door can be any suitable known sterilizer door constructed and mounted to provide an air-tight seal between the chamber 16 and the external environment. The door is preferably provided with an automatic locking assembly (not shown) or any suitable locking assembly which will satisfy safety requirements.

Vapor jacket 20 is equipped with drain 22 leading to discharge line 26 and jacket trap 24. A standard check valve 28 is positioned between the jacket trap 24 and the line to waste. The vapor passing to waste is cooled with water to a temperature which is acceptable for discharging into a conventional sewer drain.

Chamber 16 is equipped with drain 30 leading to a drain line 32 which branches into main drain line 44 and slow bleed line 34. Line 44 leads to a fast exhaust solenoid valve 38 which opens line 44 to a water cooled heat exchanger 76. Line 32 leads to a remotely positioned air detector 45 which includes a generally upwardly extending tube in which is positioned a temperature sensing means, or transducer 48. Upstream from the air detector 45, line 32 branches into a condensate drain line having a trap 36. The line 32 thereafter leads to the solenoid valve 38 for discharge through the main drain line 44 to the heat exchanger 76.

Line 34 includes a constant bleed valve 40, which is preferably a standard needle valve. The drain line temperature sensing means, or transducer 42 is positioned adjacent to drain 30 in the juncture between the branching lines upstream of trap 36 and air detector 45.

The vapor jacket 20 includes a safety relief valve 50 which opens to waste. A vapor jacket pressure guage 52 is also provided. A chamber pressure guage 54 and a transducer 90 for sensing the chamber pressure and vacuum levels are provided.

Chamber evacuation is accomplished through line 44. An ejector 84 is connected to the heat exchanger 76. Ejector 84 is supplied with water, at a uniform pressure through a water supply valve 104, a check valve 106 and a solenoid valve 108. Flow of water through the ejector 84 creates suction in the end of line 44 and drain 30 to evacuate the sterilization chamber 16.

An optional water source 80 and pump 82 may be provided when sterilizer 10 is used in locations which do not have access to pressurized water.

Heat exchanger 76 is cooled with water from the ejector 84 during evacuation or through alternate lines controlled by an exhaust cooling solenoid valve 86 and a needle valve 88.

Air is passed through filter 60 to provide sterile filtered air for stage 4 of the sterilization cycle. Filter 60 is of a type to effectively remove bacteria, dust and other undesirable particles from the air. The flow of sterile air into the chamber 16 is controlled by solenoid valve 62 and one way check valve 64.

Vapor is supplied to chamber 16 through vapor jacket 20. A main vapor supply line 72 connects a source of vapor, such as a boiler (not shown), to the vapor jacket 20. A vapor supply valve 56 and pressure regulator 74 control the flow of vapor into jacket 20. Line 68 connects jacket 20 to solenoid valve 70 which controls delivery of the vapor from the jacket 20 to inlet 66 of chamber 16.

Referring to FIG. 3, a microcomputer receives input from the temperature and pressure/vacuum transducers 42, 48 and 90, respectively. The desired pressure, vacuum and temperature levels are factory set on the appropriate logic switches to permit a comparison between the actual levels and the desired levels. When the actual level detected by the particular transducer matches the desired level set by the logic switch, the microcomputer relays the information by means of the appropriate line to the microcomputer controller. The controller in turn activates the valves which control the flow of air, vapor and water in the sterilizer 10. The controller also controls the cycle and indicates to the microcomputer that a cycle has started. Start switches and cycle time switches are provided. The controller also provides information to the L.E.D. time display. The microcomputer provides information to the L.E.D. temperature and pressure display and to the printer which records the temperature and pressure/vacuum levels at preselected intervals.

At the start of a cycle the goods, porous fabric loads, are placed into the sterilization chamber 16. The power is switched on, the door locked and the cycle started. In stage 1, the load is conditioned by removing noncondensable gases, such as air, and heating the chamber and the load to a temperature which is below a predetermined upper level by subjecting the load to a plurality of cyclic pressure/vacuum pulses. The principle behind alternate evacuation and vapor pressurization is explained in the Young Patent, discussed hereinabove, which is hereby incorporated by reference.

Referring to FIG. 1, the chamber 16 is pressurized with a condensable vapor having transferable latent heat, such as steam, which forces entrapped noncondensable gases, such as air, from the porous load. During this portion of the first pressure pulse the valve 70 which controls the delivery of vapor, or steam, from jacket 20 to chamber 16 is open. The exhaust solenoid valve 38, exhaust cooling valve 86 and the vacuum water solenoid valve 108 are open. The optional water pump 82 operates throughout the cycle when it is present. Solenoid valve 62 closes at the end of the first purge in stage 1 and remains closed until the sterilization hold portion of stage 2 of the cycle. Valve 62 is then opened and at the start of stage 3 valve 62 is closed. Valve 62 is a normally open solenoid valve. As those skilled in the art know, an electrical current to solenoid valve 62 is required to close it. During the sterilization hold portion of stage 2, the pressure in chamber 16 is high so one-way check valve 64 prevents air from entering the chamber. Opening valve 62 at this point is an energy saving feature of some varieties of sterilizers because the electrical current required to close normally open valve 62 can be turned off.

Valve 70 closes during each evacuation portion of a pulse and opens during each pressurization portion of a pulse. Exhaust valve 38 in main drain line 44 is open during the first pulse, in both the pressurization and evacuation portions. Thereafter, during stage 1, valve 38 is open only during the evacuation portion of each pulse. Valve 38 closes during all of stage 2 and opens again during all of stage 3. It opens again toward the end of stage 4 to complete the cycle and exhaust the drain lines 32, 34 and 44. Valve 108 is open each time valve 38 is open, except at the end of the cycle, to provide the necessary vacuum.

In the preferred embodiment, the controller is programmed to allow one minute for the initial pressurization from point 1 on the graph in FIG. 1 to point 2 of that graph. The pressure at point 1 is atmospheric pressure, or 0 psig. At the end of one minute of the steam pressurization, at point 2, a vacuum is drawn to about 10 inches Hg, at point 3.

During the evacuation portion of each pulse, for example, during the portion from point 2 to point 3 of the pulse from point 1 to point 3 in FIG. 1, the exhaust cooling valve 86 closes when the pressure falls to about 3-4 psig and remains closed for the remainder of the evacuation portion and the pressurization portion of the next pulse, e.g. from a point intermediate points 2 and 3 to point 4 on the graph in FIG. 1. Valve 86 continues that pattern throughout stage 1, is closed throughout stage 2 and opens again during the portion of stage 3 when the pressure falls from point 25 to point 27 at about 3-4 psig. Valve 86 thereafter remains closed.

When the chamber 16 pressure detected by transducer 90 falls to 3-4 psig intermediate points 2 and 3 on the graph in FIG. 1, the vacuum continues for at least one minute and until the vacuum level reaches at least 10 inches Hg. Both minimal evacuation time and minimal vacuum levels must be met. During the first two initial evacuation portions, at points 2 to 3 and 4 to 5, the minimal evacuation time is set at at least one minute and the minimal vacuum level is set at at least 10 inches Hg. During the following final pulses, however, the minimal vacuum levels are set at at least 20 inches Hg. A deeper vacuum may be drawn. The minimal evacuation time remains set at at least one minute.

The deeper vacuum levels drawn in the final evacuation portions, points 7 and 9 on the graph in FIG. 1, permit both full and partial loads to reach the same vacuum level. Thus, about the same amount of air will be removed from the load and the sterilization chamber. The deeper vacuum levels thus drawn aid in the accuracy of the air detector 45 because the transducer 48 will sense about the same proportions of steam to air for partial and full porous loads at a standard starting point. Because the chamber 16 and its load begin stage 2 of the cycle with the same steam to air proportions, whether there is a full or partial load, unacceptable levels of air detected during stage 2 will more likely be the result of an air leak rather than differences in the load quantity.

Following stage 1 of the cycle, the diffusion dwell sequence begins. The diffusion dwell sequence provides the stabilization of temperature between the chamber 16, the porous load and the chamber drain line temperature sensing transducer 42. Stabilization permits minimal deviation between the ambient chamber temperature and the load temperature and minimizes the lag between the temperature sensed in the chamber drain line by transducer 42 and the load temperature, thereby enhancing the effectiveness of the sterilization phase of stage 2.

The diffusion dwell phase as shown in FIG. 1, includes a sequence of steps consisting of pressure rises followed by pressure plateaus, resulting in a gradual overall pressure rise during which the condensable vapor, or steam, delivered to chamber 16 during the pressure rise has an opportunity to diffuse throughout the chamber, the load and the drain line. Any residual air in the porous load is forced out of the load and into the chamber where it can be forced into the drain during the following pressure rise. A continuous gradual pressurization period or any number of such diffusion dwell pressurization steps will be sufficient, and are within the scope of the present invention, provided the pressurization (1) allows such steam penetration through the load that the load reaches a general temperature equilibrium with the pressurized steam in the chamber and, (2) allows the load, chamber and chamber drain temperatures to stabilize during the pressure come-up to prevent superheating the chamber. The chamber ambient temperature should rise so gradually to the predetermined sterilization phase temperature that the opportunity for substantially surpassing the desired temperature is substantially eliminated.

Superheating the chamber to a temperature greater than that desired for effective sterilization is detrimental to sterilization because the drain line temperature transducer 42 may be effected by the superheat temperature which may be greater than the saturated steam temperature. Because saturated steam is necessary to effective sterilization, a reading of the higher superheat temperature will prematurely communicate temperature level satisfaction to the microcomputer and the controller, thus, prematurely starting the sterilizer hold timer. The diffusion dwell sequence of pressurization rises and plateaus avoids the superheat effect by elevating the temperature gradually and evenly throughout the relevant areas.

Figure 4:
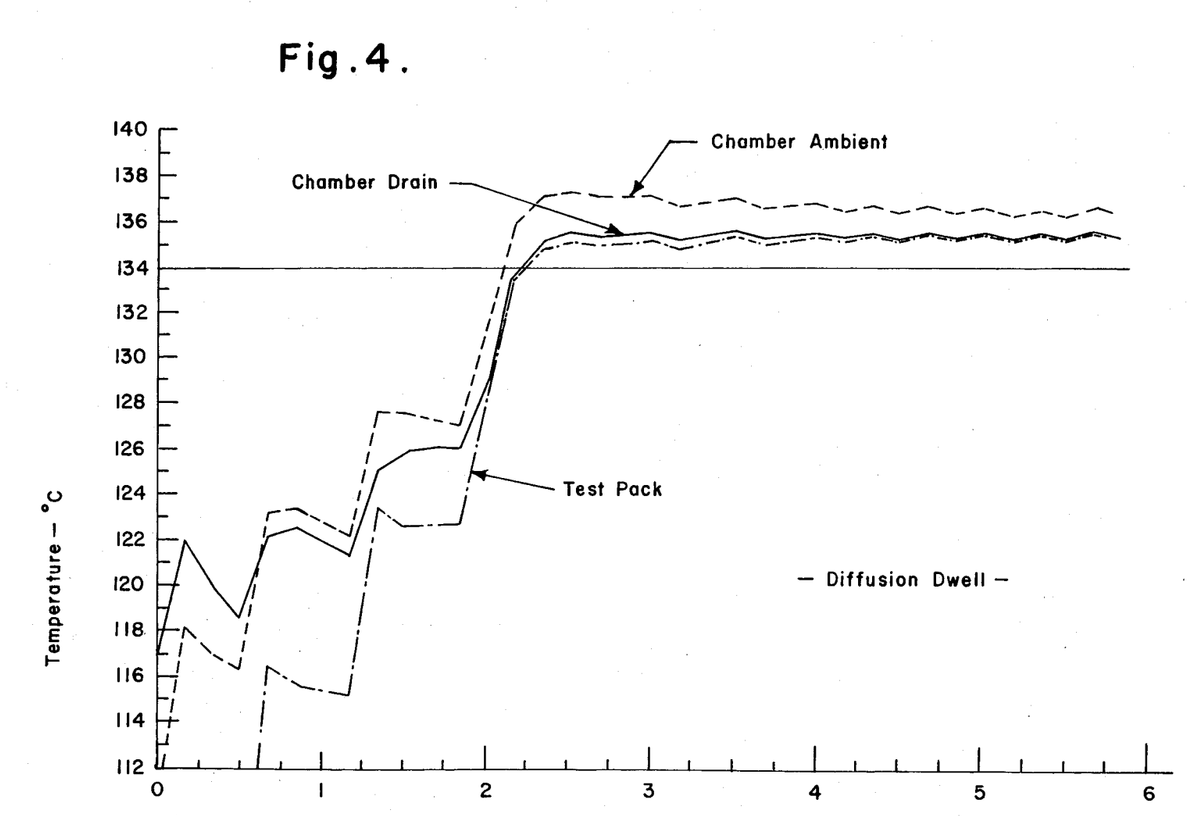
FIG. 4 is a graph of the rise in temperature over time of a porous test pack, the ambient chamber and the chamber drain during a phase of the present invention; and, FIG. 5 is a graph of the rise in temperature over time of the same locations during a phase of a prior art sterilization method.
Figure 5:
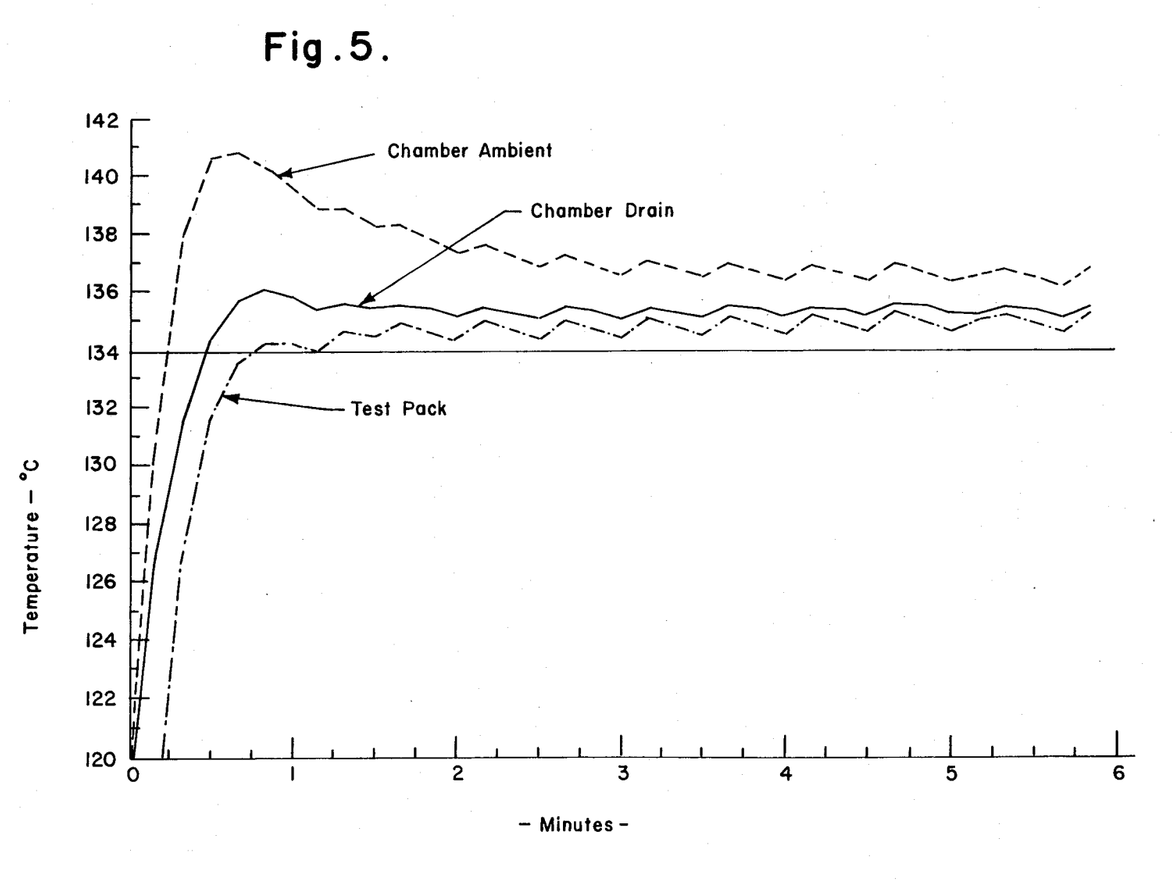

FIGS. 4 and 5 represent the result of a comparison between the prior art method of pressurization come-up and the diffusion dwell method. The rise in temperature over time of a test pack, the chamber drain and the ambient chamber during the pressurization come-up of each method were measured. The chamber was drawn to the same vacuum level prior to initiation of each method.

Referring to FIG. 4, after two minutes of the diffusion dwell come-up, when the sterilization hold phase begins, the chamber drain temperature and the test pack temperature are substantially equal.

Comparing FIG. 5 which shows the rise in temperature over time for the test pack, chamber drain and ambient chamber when the prior art method of pressurization come-up is used, there is a chamber ambient and chamber drain superheat. There is also a greater disparity between the temperatures of the three locations.

Referring then to FIG. 1, stage 2 of the sterilization cycle, in the preferred embodiment, includes the steps of elevating the chamber pressure and temperature by injecting with saturated steam, beginning at point 9 on the graph and continuing to point 11. At point 9, valve 70 is opened. At point 11, valve 70 is closed so that no more steam is admitted into chamber 16. There is a momentary pressure plateau between points 11 and 12 while the chamber is isolated.

In the graph illustrated, the suggested time for the first diffusion dwell step is forty seconds.

Thereafter, valve 70 is opened to admit more steam to increase the chamber pressure as shown, from point 12 to point 13 on the graph. A second dwell, or pressure plateau period is maintained, as shown from point 13 to point 15 on the graph in FIG. 1. The second step is also suggested to take forty seconds. There are three pressure rise and plateau steps shown in the diffusion dwell phase of stage 2 which are preferably completed in about two minutes.

At the end of the two minute diffusion dwell phase, valve 70 opens to admit steam to elevate the temperature and pressure to the desired sterilization temperature. When the desired temperature is reached the three and one-half minute sterilization hold phase begins. Steam is admitted into the chamber 16 intermittently during this phase to maintain the temperature between about 134° and 138° C., preferably about 136° C. A higher temperature maintained for a shorter period may also be effective. Those skilled in the art will recognize the interrelationship between the saturated steam temperature and the duration of sterilization necessary for effective sterilization and can adjust the sterilization hold phase accordingly.

At the end of stage 2, valve 70 is closed, and valves 38 and 108 are opened for stage 3, the drying phase of the cycle. During stage 3 the chamber 16 is evacuated and a relatively deep vacuum is maintained for a predetermined time to dry the load.

At the end of stage 3, air is admitted to the chamber 16 after passing through filter 60 and valve 62 to bring the chamber 16 to atmospheric pressure.

During the sterilization hold phase, the load temperature will rise to the sterilizing temperature with minimal delay relative to the chamber drain temperature, as detected by the transducer 42, unless unacceptable amounts of noncondensable gases are present. Air may leak into the chamber 16 due to an ineffective seal on the chamber door or a leakage in the sterilizer piping. Carbon dioxide or other noncondensable gases can leak into the chamber 16 with the steam due to inefficiencies in the boiler or other vapor source.

If there is an air leak, for example, the remote temperature transducer 48 in air detector 45 will sense a leak that is beyond acceptable limits. It has been established that a leak rate greater than 1 mm/min. at 50 mm Hg is unacceptable. Therefore, the air detector must be sensitive enough to detect levels as low as 1 mm/min.

The air detector 45 begins operating at the start of stage 2. Main drain line 44 is closed by solenoid valve 38. Steam escaping through drain 30 flows through drain line 32 to trap 36. Air detector 45 is positioned in a remote location relative to vapor jacket 20 and chamber 16 so that the ambient air surrounding air detector 45 is cool. Steam escaping through line 32 is cooled and condenses. The condensate flows to trap 36. If any noncondensable gas, such as air is present, it will accumulate in the upwardly extending pipe section which forms air detector 45. The decrease of air and other noncondensable gases in the load and chamber during the diffusion dwell phase causes an increase in the amount of noncondensable gases accumulated in the air detector 45.

The proportion of air to steam in the air detector 45 is greater therefore, than the air to steam proportion in the chamber 16 at that time. As more air accumulates, the cool ambient air surrounding the air detector 45 causes the accumulated air to cool. The air detector temperature may rise to a maximum and then may fall several degrees as air accumulates. The load temperature, on the other hand, remains stable or rises.

When the transducer 48 senses a preselected temperature effective for indicating the presence of too great a quantity of air or other noncondensable gases in the chamber 16, the microcomputer will automatically fail the cycle. Unlike the prior art air detection arrangements which assume eventual sterilization, the air detection method of the present invention fails the cycle when unacceptable air leak levels are sensed. In the preferred embodiment, the cycle will fail when a temperature of between about 110° and 114° C. is sensed by transducer 48. The exact temperature predetermined and preprogrammed to fail a cycle may vary from sterilizer to sterilizer due to differences such as the volume of the air detector or the depth of insertion of the temperature sensing means.

The steam sterilization cycle of the present invention, particularly the diffusion dwell phase and the improved conditioning, or air removal stage, promotes maximum air removal and expeditious steam penetration into full and partial porous loads alike, thus improving the accuracy and effectiveness of the sterilization cycle. Furthermore, the sterilization cycle of the present invention provides an air detection system of increased sensitivity and accuracy.

What is claimed is:

1. A method of increasing the temperature and pressure within a sealable chamber wherein a porous load is disposed for processing and from both of which noncondensable gases have been substantially removed comprising:

after sealing said chamber, subjecting said chamber to a plurality of pressurization steps wherein a condensable vapor having transferable latent heat is so injected into said chamber that (a) said plurality of pressurization steps are sufficient to so gradually elevate the temperature and pressure within said chamber to a predetermined temperature and pressure effective for processing said porous load that the opportunity for substantially surpassing said predetermined temperature is substantially eliminated, and (b) said plurality of pressurization steps are sufficient to permit such penetration of said porous load by said vapor that said porous load reaches a general temperature equilibrium with said vapor in said chamber at about the same time as said chamber reaches said predetermined temperature to avoid superheating said chamber relative to said porous load;

each said pressurization step including a pressure rise during which said vapor is injected into said chamber followed by a pressure plateau, greater than the previous pressure plateau, during which said chamber is isolated and said vapor is not injected into said chamber to permit said vapor injected during said pressure rise to penetrate said porous load to displace noncondensable gases and to permit said chamber and said porous load temperatures to stabilize.

2. A method as recited in claim 1 further comprising a conditioning stage for substantially removing noncondensable gases from said chamber and said porous load, said conditioning stage comprising:

subjecting said chamber and said load to a plurality of cyclic pressure pulses below an upper pressure level related to said predetermined temperature by injecting said vapor into said chamber and evacuating said chamber, each cyclic pressure pulse including a vapor injecting phase during which the pressure is increasing and an evacuating phase during which the pressure in said chamber is decreasing;

said evacuating phases of said plurality of pressure pulses including at least one initial evacuating phase during which the pressure in said chamber is decreased to a first lower pressure level and at least one final evacuating phase during which the pressure in said chamber is decreased to a second lower pressure level which is lower than said first lower pressure level.

3. A method as recited in claim 1 wherein said predetermined temperature is a temperature effective for sterilizing said porous load.

4. A method as recited in claim 3 wherein said condensable vapor is steam.

5. A method as recited in claim 4 wherein said predetermined temperature is between about 134° C. and 138° C. and said plurality of pressurization steps are completed in about two minutes.

6. In a method for sterilizing porous loads in a sterilizer having a sealable pressure chamber and associated piping wherein a condensable vapor having transferable latent heat is employed as a sterilizing agent, said method having at least a conditioning step during which noncondensable gases are removed from said chamber and said load, followed by a sterilization step an improvement in said sterilization stem comprising:

subjecting said chamber to a plurality of pressurization steps wherein said vapor is so injected into said chamber that (a) said plurality of pressurization steps are sufficient to so gradually elevate the temperature and pressure effective for sterilizing said porous load that the opportunity for substantially surpassing said predetermined temperature is substantially eliminated and (b) said plurality of pressurization steps are sufficient to permit such penetration of said porous load by said vapor that said porous load reaches a general temperature equilibrium with said chamber at about the same time as said chamber reaches said predetermined temperature to avoid superheating said chamber relative to said porous load, each said pressurization step including a pressure rise during which said vapor is injected into said chamber followed by a pressure plateau, greater than the previous pressure plateau, during which said chamber is isolated and said vapor is not injected into said chamber to permit said vapor injected during said pressure rise to penetrate said porous load to displace noncondensable gases and to permit said chamber and said porous load temperature to stabilize; and holding said chamber at said predetermined temperature for a predetermined period of time sufficient to sterilize said porous load.

7. A method as recited in claim 6 further comprising a drying stage following said sterilization stage during which a vacuum is maintained for a period effective for drying said load, and an air admission stage following said drying stage during which sterile air is admitted to said chamber to bring said chamber to atmospheric pressure.

8. A method as recited in claim 6 wherein said vapor is steam.

9. A method as recited in claim 6 further comprising an improvement in said conditioning stage, said improvement comprising:
   subjecting said chamber and said load to a plurality of cyclic pressure pulses below an upper pressure level related to said predetermined tempeature by injecting said vapor into said chamber and evacuating said chamber, each cyclic pressure pulse including a vapor injecting phase during which the pressure is increasing and an evacuating phase during which the pressure in said chamber is decreasing;
   said evacuation phases of said plurality of pressure pulses including at least one initial evacuating phase during which the pressure in said chamber is decreased to a first lower pressure level and at least one final evacuation phase during which the pressure in said chamber is decreased to a second lower pressure level which is lower than said first lower pressure level.

10. A method as recited in claim 9 wherein said associated piping includes a remote section and said method further comprises steps for detecting and responding to unacceptable levels of noncondensable gas in a fluid in said chamber during said sterilization stage, said fluid including at least said vapor, said noncondensable gas detecting step comprising:
   communicating said fluid within said chamber to said remote section during said sterilization stage;
   condensing said vapor from said fluid and discharging said condensate from said remote section as said fluid is communicated to said remote section so that any noncondensable gas within said fluid accumulates in said remote section;
   measuring the temperature of said accumulating noncondensable gas within said remote section; and
   employing the measured noncondensable gas temperature to automatically fail said sterilization cycle when the measured noncondensable gas temperature equals a preselected temperature effective for indicating the presence of a predetermined unacceptable level of noncondensable gas in said chamber.

11. A method as recited in claim 10 wherein said predetermined unacceptable level of noncondensable gas is produced by a leak greater than 1 mm Hg/min at 50 mm Hg.

12. A method as recited in claim 10 wherein said vapor is condensed by surrounding said remote section with atmospheric air sufficiently cool to condense said vapor.

* * * * *

UNITED STATES PATENT AND TRADEMARK OFFICE
CERTIFICATE OF CORRECTION

PATENT NO.   :   4,687,635
DATED        :   August 18, 1987
INVENTOR(S)  :   Kristine M. Kaehler et al.

It is certified that error appears in the above—identified patent and that said Letters Patent is hereby corrected as shown below:

Col. 1, line 6, delete "steam".

Col. 1, line 10, delete "stabilization" and substitute therefor --sterilization--.

Col. 1, line 17, delete "method" and substitute therefor --methods--.

Col. 1, line 66, delete "remain" and substitute therefor --remains--.

Col. 3, line 65, delete "3" and substitute therefor --2--.

Col. 10, line 41, delete "stem" and substitute therefor --step--.

Signed and Sealed this

Twenty-ninth Day of March, 1988

Attest:

DONALD J. QUIGG

*Attesting Officer*    *Commissioner of Patents and Trademarks*